United States Patent
Deckert et al.

(10) Patent No.: US 8,461,396 B2
(45) Date of Patent: Jun. 11, 2013

(54) PROCESS FOR PURIFYING AQUEOUS GLYOXAL SOLUTIONS

(75) Inventors: Petra Deckert, Bammental (DE); Peter Groll, Dannstadt-Schauernheim (DE); Bernd Rumpf, Hockenheim (DE); Christian Horn, Ruessingen (DE)

(73) Assignee: BASF SE (DE)

( * ) Notice: Subject to any disclaimer, the term of this patent is extended or adjusted under 35 U.S.C. 154(b) by 74 days.

(21) Appl. No.: 13/251,713

(22) Filed: Oct. 3, 2011

(65) Prior Publication Data
US 2012/0116129 A1 May 10, 2012

Related U.S. Application Data

(60) Provisional application No. 61/388,638, filed on Oct. 1, 2010.

(51) Int. Cl.
*C07C 45/80* (2006.01)
(52) U.S. Cl.
USPC ........................................................ 568/492
(58) Field of Classification Search
USPC ........................................................ 568/492
See application file for complete search history.

(56) References Cited

U.S. PATENT DOCUMENTS

| 3,270,062 A | | 8/1966 | Merz et al. | |
| 3,860,656 A | * | 1/1975 | McCain et al. | 568/492 |
| 7,226,567 B1 | | 6/2007 | Olbert et al. | |

FOREIGN PATENT DOCUMENTS

| DE | 19 23 048 | 11/1969 |
| DE | 34 02 733 | 8/1984 |
| EP | 1 169 119 | 1/2002 |
| GB | 1272592 | 5/1972 |

* cited by examiner

*Primary Examiner* — Sikarl Witherspoon
(74) *Attorney, Agent, or Firm* — Novak Druce Connolly Bove + Quigg LLP

(57) ABSTRACT

A process for purifying an aqueous glyoxal solution comprising at least one acid by extractive acid removal, comprising
i) mixing and dispersion of the aqueous glyoxal solution with an ion exchanger solution comprising a tertiary amine and an organic solvent,
ii) phase separation and removal of the ion exchanger solution laden with the acid from the aqueous glyoxal solution, and
iii) regeneration of the ion exchanger solution by contacting with a basic compound for neutralization of the acid and removal of the basic compound,
iv) mixing and dispersion of the ion exchanger solution with water to obtain a dispersion of water and ion exchanger solution,
v) Phase separation and removal of the aqueous phase from the ion exchanger solution in such a way that the content of the aqueous phase of the regenerated ion exchanger solution is <1% by weight, and recycling of the ion exchanger solution into step i).

6 Claims, No Drawings

PROCESS FOR PURIFYING AQUEOUS GLYOXAL SOLUTIONS

CROSS-REFERENCE TO RELATED APPLICATIONS

This application claims the benefit of U.S. Provisional Application 61/388,638, filed on Oct. 1, 2010, which is incorporated by reference.

BACKGROUND OF THE INVENTION

The present invention relates to a process for purifying aqueous glyoxal solutions comprising at least one acid with an ion exchanger solution and to the aqueous glyoxal solutions obtainable by this process.

Glyoxal is used, for example, as an auxiliary component in the textile or paper industry. Glyoxal is prepared typically by oxidation of acetaldehyde of by oxydehydrogenation of the corresponding glycol over a catalytic fixed bed. The catalyst used is, for example, phosphorus-doped copper. The aqueous glyoxal solutions obtained in this process have by-products which have to be removed before the further use thereof. Typical by-products are formaldehyde, glycolaldehyde, formic acid, acetic acid, and nonvolatile acids such as glyoxylic acid, glycolic acid and oxalic acid. The glyoxal prepared from glycol by oxydehydrogenation comprises generally not more than 2% by weight of acid. For the commercial use of the glyoxal, however, acid numbers of <5 mg KOH/g are required.

For removal of the abovementioned acids, in particular of the nonvolatile acids, various processes are described in the prior art. U.S. Pat. No. 3,270,062 describes a process for purifying aqueous glyoxal solutions by treating the glyoxal solution with a solid ion exchanger. This process has the disadvantage of batchwise operation. Moreover, the ion exchangers have to be regenerated frequently owing to the high acid values of the aqueous glyoxal solutions used. For this reason, considerable amounts of dilute glyoxal solutions are obtained in this process, and so the process described in U.S. Pat. No. 3,270,062 cannot be operated in an economically viable manner.

It is additionally known that acidic impurities can be removed from aqueous glyoxal solutions by treating them with a solution of high molecular weight tertiary amines or of quaternary ammonium salts in bicarbonate form in an organic solvent. In this process, the two solutions are conducted in countercurrent to one another in a multistage extraction column. This achieves continuous purification, but long residence times are required. Moreover, in this process, avoidance of excessively great glyoxal losses necessitates reextraction of the organic phase with water. The result of this is that this process is unattractive.

Workup of the glyoxal prepared by oxidation of acetaldehyde or by oxydehydrogenation is absolutely necessary since the glyoxal solutions obtained by this process have a strong yellow color. For the commercially used glyoxal solutions, typically color numbers of <200 Apha are required in the end product.

DE 34 02 733 describes a process for purifying aqueous glyoxal solutions by extracting the acids present in the glyoxal solution with a solution of a tertiary amine in an organic solvent.

In the process described therein, aqueous glyoxal solutions having an acid number of <5 mg KOH/g and a low color number are obtained. The glyoxal solutions obtainable by this process thus meet specifications required for commercial glyoxal solutions. In the process described in DE 34 02 733, the glyoxal loss into the solution of tertiary amine and organic solvent is additionally low.

The ion exchanger solution is regenerated in a manner known per se by contacting with basic compounds such as sodium hydroxide, potassium hydroxide and sodium bicarbonate, and neutralization of the acid bound in the ion exchanger solution. Typically, the neutralized ion exchanger solution still comprises considerable amounts of salts formed in the neutralization, which would be transferred to the glyoxal solution in the acid extraction and would impair the product quality. Therefore, before the regenerated ion exchanger is used again as an extractant, a salt wash with water is carried out.

A problem in the acid extraction is the glyoxal loss through glyoxal transferred to the extractant phase. It is partly degraded by Canizarro reaction in the course of regeneration of the ion exchanger solution; the degradation products pass into the wastewater.

BRIEF SUMMARY OF THE INVENTION

It is an object of the present invention to provide a process for purifying aqueous glyoxal solution, which is characterized by a low glyoxal loss.

The object is achieved by a process for purifying an aqueous glyoxal solution comprising at least one acid by extractive acid removal, comprising the steps of i) mixing and dispersion of the aqueous glyoxal solution with an ion exchanger solution comprising 20 to 60% by weight of a tertiary amine and 80 to 40% by weight of an organic solvent which does not have unlimited miscibility with water at a temperature of 30 to 100° C., ii) phase separation and removal of the ion exchanger solution laden with the acid from the aqueous glyoxal solution at temperatures of 30 to 100° C., and iii) regeneration of the ion exchanger solution by contacting with a basic compound for neutralization of the acid and removal of the basic compound, iv) mixing and dispersion of the ion exchanger solution with water to free it of salts formed in the neutralization to obtain a dispersion of water and ion exchanger solution, v) phase separation and removal of the aqueous phase from the ion exchanger solution, and recycling of the ion exchanger solution into steps i), which comprises phase separation and removal of the aqueous phase in step v) in such a way that the content of the aqueous phase of the regenerated ion exchanger solution obtained in step v) is <1% by weight.

DETAILED DESCRIPTION OF THE INVENTION

The content of the aqueous phase is the amount of the amount of undissolved extraneous phase (which is removable in principle) remaining in the ion exchanger solution, and does not include the amount of water dissolved homogeneously in the ion exchanger solution.

It has been found that, surprisingly, a minimum water content in the ion exchanger solution obtained after the regeneration can minimize the glyoxal loss in the subsequent acid extraction step.

In step i) of the process according to the invention, aqueous glyoxal solutions which, as a result of the preparation, comprise at least one acid as a by-product are mixed with an ion exchanger solution. Aqueous glyoxal solutions are generally obtained by oxidation of acetaldehyde or by oxydehydrogenation of monoethylene glycol over a catalyst. For example, aqueous glyoxal solutions obtainable in accordance with the process described in DE 19 23 048 by oxydehydrogenation over a fixed catalyst bed comprising phosphorus-doped copper as a catalyst are treated in accordance with the invention.

The aqueous glyoxal solution can also be obtained by the processes described in DE 500 04 079 and EP 1 169 119. For this purpose, monoethylene glycol is converted to the gas phase in a suitable evaporator and dehydrogenated in a reactor in the presence of oxygen. The gaseous product mixture leaving the reactor, which comprises other by-products as well as glyoxal, is cooled. This condenses out the condensable components, such as water and glyoxal, and by-products such as formaldehyde, glycolaldehyde, formic acid, and nonvolatile acids such as glyoxylic acid, glycolic acid and oxalic acid. The further workup of the product stream is effected by stripping out low-boiling components, such as formaldehyde, formic acid and acetic acid, by means of steam. The aqueous glyoxal solutions thus obtained still comprise nonvolatile acids such as glyoxylic acid, glycolic acid and oxalic acid. The glyoxal solutions obtainable by the processes according to DE 500 04 079 and EP 1 169 119 are also particularly suitable for use in the process according to the invention.

The aqueous glyoxal solutions used in step i) thus comprise at least one acid selected from the group consisting of formic acid, acetic acid, glyoxylic acid, glycolic acid and oxalic acid or mixtures of two or more of the aforementioned acids, in a concentration in the range from 0.2 to 2% by weight, based on the total weight of the aqueous glyoxal solution.

The acid numbers of the aqueous glyoxal solutions used in the process according to the invention can vary within wide ranges. Preference is given, however, to aqueous glyoxal solutions which have acid numbers of $\leq$100 mg KOH/g, preferably $\leq$50 mg KOH/g and more preferably $\leq$30 mg KOH/g.

The glyoxal content of the aqueous glyoxal solutions used in the process according to the invention is also uncritical and can vary within wide ranges. In general, however, aqueous glyoxal solutions with a glyoxal content of $\leq$55% by weight, preferably $\leq$50% by weight and more preferably $\leq$45% by weight are used, where each percentage by weight is based on the total weight of the aqueous glyoxal solution used. The glyoxal content of the solutions used in the process according to the invention is generally at least 30% by weight, preferably at least 35% by weight, more preferably at least 38% by weight. For example, the glyoxal concentration of the solution used is 38 to 45%.

The aqueous glyoxal solution is mixed with an ion exchanger solution in step i). An ion exchanger solution in the context of the present invention is understood to mean a mixture which comprises at least one tertiary amine and an organic solvent which does not have unlimited miscibility with water.

Suitable tertiary amines are straight-chain or branched aliphatic amines having molecular weights of 300 to 600 g/mol. Preferred tertiary amines are trioctylamine, trinonylamine, tridecylamine and tridodecylamine. It is also possible to use mixtures of two or more of the preferred tertiary amines. In addition, it is also possible to use one or more of the preferred tertiary amines in a mixture with one or more further amines. Particular preference is given to mixtures of two tertiary amines selected from trioctylamine, trinonylamine, tridecylamine and tridodecylamine. Especially preferred are mixtures of trioctylamine and tridecylamine.

Useful organic solvents which do not have unlimited miscibility with water include all organic solvents which do not form a true solution in every ratio with water under standard conditions and do not react with glyoxal under the conditions which exist in the extraction. Preferred organic solvents are straight-chain or branched primary, secondary or tertiary alcohols which have more than 3 carbon atoms and are not miscible with water in all ratios. Preference is given to aliphatic alcohols having 3 to 15 carbon atoms, particular preference to aliphatic alcohols having 8 to 13 carbon atoms. Especially preferred are pentanol, hexanol, 2-ethylhexanol, octanol, decanol and isodecanol. The organic solvents used which do not have unlimited miscibility with water may also be mixtures of the aforementioned solvents.

The ion exchanger solution comprises generally 20 to 60% by weight, preferably 30 to 50% by weight, of at least one tertiary amine, and 80 to 40% by weight, preferably 70 to 50% by weight, of an organic solvent which does not have unlimited miscibility with water, based in each case on the total weight of the ion exchanger solution.

In step i) of the process according to the invention, the aqueous glyoxal solution is mixed with the ion exchanger solution. The mixing is effected at temperatures of 30 to 100° C., preferably of 30 to 80° C. and more preferably of 30 to 60° C. The volume ratio of aqueous glyoxal solution and ion exchanger solution is freely selectable. Preference is given to volume ratios between 10:1 and 1:3.

The aqueous glyoxal solution can be mixed with the ion exchanger solution in any known mixing apparatus. It has been found that the residence time of the two solutions should be at a minimum so that the equilibrium concentration of glyoxal in the ion exchanger phase cannot be established. Residence time is understood to mean the time interval during which the aqueous glyoxal solution and ion exchanger solution are present being mixed in the mixing apparatus. The phases are being mixed essentially for as long as the mixing and dispersion operation is maintained. A minimum residence time can minimize the transfer of glyoxal from the aqueous glyoxal solution to the ion exchanger solution and hence the loss of glyoxal. Suitable residence times are below 5 minutes, preferably in the range from 1 second to 2 minutes, especially preferably in the range from 1 sec to 20 sec.

The acids present in the aqueous glyoxal solution are bound to the tertiary amines present in the ion exchanger solution. This gives rise to an ion exchanger solution laden with the bound acid, which comprises acids present in the glyoxal solution in bound form. Suitable mixing apparatus enables dispersion with minimum backmixing with a very short residence time, while simultaneously enabling good phase separation. The two solutions are preferably mixed in one stage through the simultaneous introduction of aqueous glyoxal solution and ion exchanger solution into the mixing apparatus. In a preferred embodiment, a static mixer is used for this purpose. In a further preferred embodiment, an inline mixer or an aperture plate mixer is used.

In step ii), the phases are separated into an extracted aqueous glyoxal solution which has been substantially freed of acids and the ion exchanger solution laden with the acid. The separation and removal can be effected in any desired separating apparatus, such as phase separator, centrifuge or phase separator in combination with coalescence filter.

The coalescence filter may be connected upstream of the phase separator or integrated into the phase separator. The phase separator may comprise internals such as knits, random packings and/or plates as separating aids. The phase separation can be undertaken at temperatures of 30 to 100° C., preferably at 30 to 80° C. and more preferably at 30 to 60° C.

In a further step, the extracted aqueous glyoxal solution obtained in step ii) can be purified further. It has been found that the above-described removal of the ion exchanger solution in step ii) is not always complete and that small amounts of tertiary amine and of the solvent from the ion exchanger solution remain in the extracted aqueous glyoxal solution.

To remove the residual content of tertiary amine and solvent, the extracted aqueous glyoxal solution from step ii) is cooled to temperatures of <30° C., preferably to temperatures in the range from 10 to 25° C. This results in further separation of tertiary amine and possibly or organic solvent.

Optionally, further by-products from the aqueous glyoxal solution are removed by means of an absorbent after the acid extraction.

The separated tertiary amine can be removed by any known separation process. Suitable separation processes have been described above. Preference is given to removal by a coalescence filter with downstream phase separator or by a phase separator with integrated coalescence filter or by a centrifuge.

Especially preferably, step ii) is performed with a coalescence filter with downstream phase separator or with a phase separator with integrated coalescence filter. The phase separation is improved by passing the dispersion through the coalescence filter. Preferred materials for the coalescence filter are polymers, especially polypropylene and polyethylene or mixtures thereof.

In step iii), the ion exchanger solution is regenerated by contacting with a basic compound for neutralization of the bound acid.

Suitable basic compounds are, for example, sodium hydroxide, potassium hydroxide and sodium bicarbonate. These are added generally in the form of the aqueous solutions thereof. In general, they comprise 1 to 30% by weight, preferably 2 to 15% by weight, for example 5% by weight, of the basic compound.

This involves adding the solution of the basic compound and dispersing it with the ion exchanger solution in a suitable mixing unit and at a temperature of 30 to 100° C. In general, the weight ratio of solution of the basic compound:ion exchanger solution is 0.02:1 to 1:1. The solution of the basic compound generally forms the disperse phase. The residence time is generally <20 min, preferably 0.1 to 15 min, more preferably 2 to 8 min.

Suitable dispersing units are, for example, a mixing pump, a static mixer or a stirred vessel.

In step iv), the ion exchanger solution is mixed with water to free it of salts formed in the neutralization.

This involves adding water and dispersing it with the ion exchanger solution in a suitable mixing unit and at a temperature of 30 to 100° C. In general, the weight ratio of water:ion exchanger solution is 0.1:1 to 1:1. Water forms the disperse phase. The residence time is generally <20 min, preferably 0.1 to 15 min, more preferably 2 to 8 min.

Suitable dispersing units are likewise, for example, a mixing pump, a static mixer or a stirred vessel.

In step v), the phases are separated and the aqueous phase is removed from the ion exchanger solution. The ion exchanger solution removed is subsequently recycled back into the acid extraction step i).

The essential feature of the invention is that the phase separation and the removal of the aqueous phase comprising the dissolved salts in step v) are effected such that the content of the aqueous phase in the regenerated ion exchanger solution obtained in step v) is <1% by weight. The content of the aqueous phase is preferably <0.5% by weight, more preferably <0.2% by weight, especially <0.1% by weight.

The content of the aqueous extraneous phase is found by determining the total water content of the ion exchanger solution and the concentration of water dissolved homogeneously in the ion exchanger solution, in each case by the Karl Fischer method.

The separation of the dispersion from step iv) and removal of the aqueous phase can be effected in an effective separation apparatus, such as a phase separator with separating internals such as knits or plates, or in a phase separator in combination with an upstream coalescence filter, in a centrifuge, a hydrocyclone or electrostatic separator. The coalescence filter may be a separate apparatus connected upstream of the phase separator or be integrated into the phase separator. Passing the dispersion through the coalescence filter brings about an improved phase separation. Suitable materials for the coalescence filter are all materials which are stable to the ion exchanger solution. Suitable materials are, for example, fibers of phenol resin, glass, metal or cotton. The dispersion step iv) and the separation step v) can also be performed together in an extraction column.

The invention is illustrated in detail by the examples.

EXAMPLES

Example 1

Influence of the Glyoxal Content in the Feed to the Acid Extraction on the Solubility of Glyoxal in the Ion Exchanger Solution In a stirred vessel, the ion exchanger solution consisting of 40% Hostarex A327 (mixture of 50% tridodecylamine and 50% trioctylamine from Clariant) and 60% isodecanol was dispersed at 45° C. with acid-containing glyoxal solutions from production operation, in each case with addition of 0.5 kg of ion exchanger solution based on 1 kg of glyoxal solution. The experiments were conducted with glyoxal solutions which had different glyoxal contents between 30 and 42% by weight. After 10 min of stirring time at constant speed, samples were taken from the stirred vessel, and after the phase separation the glyoxal concentrations in the clear glyoxal phases were analyzed.

TABLE 1

| Glyoxal concentration before extraction [% by wt.] | Glyoxal concentration of the extracted glyoxal phase [% by wt.] | Reduction in the glyoxal concentration [% by wt.] | Glyoxal loss [%] |
| --- | --- | --- | --- |
| 41.1 | 38.0 | 3.5 | 8.4 |
| 37.8 | 34.8 | 3.1 | 8.1 |
| 30.4 | 28.0 | 2.4 | 8.0 |

The equilibrium concentrations of glyoxal in the ion exchanger solution are higher when a more highly concentrated glyoxal solution is extracted. In other words, the higher the glyoxal concentration in the feed to the extraction, the higher the reduction in the glyoxal concentration at equilibrium and hence the loss.

Examples 2 and 3

Influence of Aqueous Extraneous Phase in the Ion Exchanger Solution on the Glyoxal Loss in the Acid Extraction with Short Dispersion Times In a stirred vessel, the ion exchanger solution consisting of 40% Hostarex A327 (mixture of 50% tridodecylamine and 50% trioctylamine from Clariant) and 60% isodecanol was dispersed at 45° C. with acid-containing glyoxal solutions from production operation, in each case with addition of 0.5 kg of ion exchanger solution based on 1 kg of glyoxal solution. In the experiments, 5% by weight of water based on the ion exchanger phase was additionally added. In one experiment, the water was added before the dispersion of the glyoxal phase, as a result of which the feed concentration decreased from 41.6 to 40.4% by weight of glyoxal. In the second experiment, the same amount of water was dispersed with the ion exchanger phase before the aqueous glyoxal phase was added. After stirring times of 0.5 and 2 min at constant speed, samples of the dispersion were taken from the stirred vessel, and the immediate phase separation by centrifugation was followed by analysis of the acid numbers by means of titration and glyoxal concentrations in the clear glyoxal phases. The data are listed in table 2 below.

TABLE 2

| | Addition of 5% by weight of water before the dispersion to the | Stirring time [min] | Acid number in the glyoxal phase [mg KOH/g] | Glyoxal concentration [% by wt.] | Glyoxal loss [%] |
|---|---|---|---|---|---|
| Example 2 | glyoxal solution | 0.5 | 0.52 | 40.0 | 1.0 |
| | | 2 | 0.31 | 39.6 | 1.9 |
| Example 3 | ion exchanger solution | 0.5 | 0.35 | 39.9 | 1.3 |
| | | 2 | 0.36 | 39.2 | 2.9 |

The acids were extracted rapidly. Acid numbers less than 1 mg KOH/g were already attained at dispersion times of 0.5 min. The glyoxal losses after a dispersion time of 0.5 min were much lower than at equilibrium with a dispersion time of 10 min.

When the additional water was dispersed in the ion exchanger solution before the dispersion of glyoxal solution and ion exchanger solution, the loss of glyoxal rose because the initially higher concentration of glyoxal in the glyoxal solution resulted in more glyoxal being extracted into the ion exchanger solution. In this case, the coarse separation of the two phases also took longer at >105 min than when the additional water was added to the glyoxal solution (coarse separation time 45 min). In other words, inadequate phase separation in the wash of the neutralized ion exchanger solution leads to a deterioration in the phase separation in the acid extraction, as a result of which the glyoxal loss rise.

Example 4

Phase Separation of Regenerated Ion Exchanger Solution and Wash Wastewater by Means of Coalescence Filters In a stirred vessel, neutralized ion exchanger solution from a production operation consisting of 40% Hostarex A327 (mixture of 50% tridodecylamine and 50% trioctylamine from Clariant) and 60% isodecanol was dispersed at 45° C. with demineralized water, with addition of 0.4 kg of demineralized water based on 1 kg of neutralized ion exchanger solution. The dispersion was separated by means of cotton coalescence filters, fineness 25 pm. The amount of extraneous phase in the ion exchanger solution was found by using the Karl Fischer method to determine the total water content of the ion exchanger solution (including the residues of aqueous extraneous phase). The results are shown in table 3.

TABLE 3

Measured extraneous phase contents in the neutralized and washed ion exchanger phase after flow though the coalescence filter at different loadings

| Dispersion flow rate [kg/h cm of candle] | Extraneous phase [% by wt.] |
|---|---|
| 1.02 | 0.01 |
| 1.86 | 0.05 |
| 3.32 | 0.14 |

If no coalescence filter is used for the phase separation, the water phase content in the neutralized and washed ion exchanger phase at a power input of 4 kW during the dispersion after a phase separation time of 10 min is 5% by weight.

The invention claimed is:

1. A process for purifying an aqueous glyoxal solution comprising at least one acid by extractive acid removal, comprising the steps of
   i) mixing and dispersing the aqueous glyoxal solution with an ion exchanger solution comprising 20 to 60% by weight of tertiary amine and 80 to 40% by weight of an organic solvent which does not have unlimited miscibility with water at a temperature of 30 to 100° C.,
   ii) phase separating and removing the ion exchanger solution laden with the acid from the aqueous glyoxal solution at a temperature of 30 to 100° C.
   iii) regenerating the ion exchanger solution by contacting with a basic compound for neutralization of the acid and removal of the basic compound,
   iv) mixing and dispersing of the ion exchanger solution with water to free it of salts formed in the neutralization to obtain a dispersion of water and ion exchanger solution, and
   v) phase separating and removing the aqueous phase from the ion exchanger solution, and recycling the ion exchanger solution into step i), wherein the aqueous phase in step v is phase separated and removed in such a way that the content of the aqueous phase of the regenerated ion exchanger solution obtained in step v) is <1% by weight.

2. The process according to claim 1, wherein the residence time during which the aqueous glyoxal solution and the ion exchanger solution are being mixed in step i) is 1 sec to 20 sec.

3. The process according to claim 1, wherein the dispersion of water and ion exchanger solution in step v) is passed through a coalescence filter for phase separation.

4. The process according to claim 2, wherein the dispersion of water and ion exchanger solution in step v) is passed through a coalescence filter for phase separation.

5. The process according to claim 1, wherein the glyoxal content of the aqueous glyoxal solution used in step i) is 38 to 45% by weight.

6. The process according to claim 4, wherein the glyoxal content of the aqueous glyoxal solution used in step i) is 38 to 45% by weight.

* * * * *